(12) United States Patent
Beeby et al.

(10) Patent No.: US 10,548,696 B2
(45) Date of Patent: Feb. 4, 2020

(54) METHOD OF MANUFACTURING AN ARTICLE

(71) Applicant: RENISHAW PLC, Wotton-under-Edge, Gloucestershire (GB)

(72) Inventors: David Beeby, Wotton-under-Edge (GB); Mark Forman, Wotton-under-Edge (GB)

(73) Assignee: RENISHAW PLC, Wotton-under-Edge (GB)

( * ) Notice: Subject to any disclaimer, the term of this patent is extended or adjusted under 35 U.S.C. 154(b) by 148 days.

(21) Appl. No.: 15/885,900

(22) Filed: Feb. 1, 2018

(65) Prior Publication Data

US 2018/0153661 A1 Jun. 7, 2018

Related U.S. Application Data

(63) Continuation of application No. 14/399,672, filed as application No. PCT/GB2013/051208 on May 10, 2013, now Pat. No. 9,918,811.

(30) Foreign Application Priority Data

May 10, 2012 (EP) .................................. 12167523

(51) Int. Cl.
   *B22F 3/105* (2006.01)
   *B22F 3/24* (2006.01)
   (Continued)

(52) U.S. Cl.
   CPC ............ *A61C 13/0019* (2013.01); *A61C 5/77* (2017.02); *A61C 13/0013* (2013.01);
   (Continued)

(58) Field of Classification Search
   CPC ....... A61C 13/0019; A61C 5/77; A61C 13/26; A61C 13/08; A61C 13/0018;
   (Continued)

(56) References Cited

U.S. PATENT DOCUMENTS

| 4,118,301 A | 10/1978 | Mayer et al. |
| 4,662,804 A * | 5/1987 | Tokita ................... B23F 19/105 409/8 |

(Continued)

FOREIGN PATENT DOCUMENTS

| CA | 2295896 A1 | 7/2000 |
| CN | 1044308 A | 8/1990 |

(Continued)

OTHER PUBLICATIONS

Kreg Tools Website, <https://web.archive.org/web/20120104142644/http://www.kregtool.com/Shelf-Pin-Jig-Prodview.html> 2012 Year: (2012).*

(Continued)

*Primary Examiner* — Jacob J Cigna
(74) *Attorney, Agent, or Firm* — Oliff PLC (57) ABSTRACT

A method of manufacturing an article, comprising taking an article formed in an initial state via an additive manufacturing process and performing a second manufacturing process to transform the article into a second state, which comprises mounting the article in a holding device, processing at least one first feature on the article, which comprises processing at least one set of mounting features on the article, re-mounting the article via the at least one set of mounting features, and then processing at least one second feature on the article.

38 Claims, 7 Drawing Sheets

(51) Int. Cl.
  *B33Y 10/00* (2015.01)
  *B33Y 80/00* (2015.01)
  *A61C 13/00* (2006.01)
  *A61C 5/77* (2017.01)
  *A61C 13/08* (2006.01)
  *A61C 13/271* (2006.01)

(52) U.S. Cl.
  CPC ...... *A61C 13/0018* (2013.01); *A61C 13/0022* (2013.01); *A61C 13/08* (2013.01); *A61C 13/26* (2013.01); *B22F 3/1055* (2013.01); *B22F 3/24* (2013.01); *B22F 2003/247* (2013.01); *B33Y 10/00* (2014.12); *B33Y 80/00* (2014.12)

(58) Field of Classification Search
  CPC ............ A61C 13/0022; A61C 13/0013; A61C 13/0004; B22F 3/24; B22F 3/1055; B22F 2003/247; B33Y 80/00; B33Y 10/00
  See application file for complete search history.

(56) References Cited

U.S. PATENT DOCUMENTS

| | | |
|---|---|---|
| 4,801,367 A | 1/1989 | Burgess et al. |
| 4,826,580 A | 5/1989 | Masuzawa et al. |
| 5,064,521 A | 11/1991 | Stepanenko et al. |
| 5,064,731 A | 11/1991 | Miyazaki et al. |
| 5,233,744 A * | 8/1993 | Noland .................. B23K 9/04 29/402.13 |
| 5,257,460 A | 11/1993 | McMurtry |
| 5,647,704 A | 7/1997 | Turchan |
| 5,725,376 A | 3/1998 | Poirier |
| 5,813,859 A | 9/1998 | Hajjar et al. |
| 5,823,778 A | 10/1998 | Schmitt et al. |
| 5,847,958 A | 12/1998 | Shaikh et al. |
| 6,382,975 B1 | 5/2002 | Poirier |
| 6,657,155 B2 | 12/2003 | Abe et al. |
| 7,035,702 B2 | 4/2006 | Jelonek et al. |
| 7,172,724 B2 | 2/2007 | Abe et al. |
| 7,452,500 B2 | 11/2008 | Uckelmann |
| 7,740,797 B2 | 6/2010 | Abe et al. |
| 7,776,189 B2 | 8/2010 | Shrivastava et al. |
| 8,021,154 B2 | 9/2011 | Holzner et al. |
| 8,029,283 B2 | 10/2011 | Schwarz et al. |
| 8,398,396 B2 | 3/2013 | Taormina |
| 8,425,973 B2 | 4/2013 | Dunne |
| 8,502,107 B2 | 8/2013 | Uckelmann |
| 8,510,929 B2 | 8/2013 | McMurtry et al. |
| 8,590,157 B2 | 11/2013 | Kruth et al. |
| 8,739,409 B2 | 6/2014 | Vagt et al. |
| 8,778,443 B2 | 7/2014 | Uckelmann et al. |
| 8,865,033 B2 | 10/2014 | Schechner et al. |
| 8,940,402 B2 | 1/2015 | Giordano |
| 9,022,784 B2 | 5/2015 | Johansson et al. |
| 9,283,620 B2 | 3/2016 | Garcia Aparicio et al. |
| 2001/0029010 A1 | 10/2001 | Wells et al. |
| 2002/0007294 A1 | 1/2002 | Bradbury et al. |
| 2002/0137002 A1 | 9/2002 | Bodenmiller |
| 2002/0187458 A1 | 12/2002 | Dolabdjian et al. |
| 2003/0054729 A1 | 3/2003 | Lee et al. |
| 2003/0207235 A1 | 11/2003 | der Zel |
| 2004/0107019 A1 | 6/2004 | Keshavmurthy et al. |
| 2004/0217095 A1 | 11/2004 | Herzog |
| 2005/0016867 A1 | 1/2005 | Kreiskott et al. |
| 2005/0060868 A1 | 3/2005 | McMurtry |
| 2005/0084344 A1* | 4/2005 | Dods .................... B23B 47/287 408/67 |
| 2005/0106534 A1 | 5/2005 | Gahlert |
| 2005/0173258 A1 | 8/2005 | Aeby et al. |
| 2005/0186538 A1 | 8/2005 | Uckelmann |
| 2006/0105297 A1 | 5/2006 | Knapp et al. |
| 2006/0166500 A1 | 7/2006 | Manens et al. |
| 2006/0172263 A1 | 8/2006 | Quadling et al. |
| 2007/0065779 A1 | 3/2007 | Mangano |
| 2007/0122767 A1 | 5/2007 | Workman et al. |
| 2007/0154864 A1 | 7/2007 | Deer et al. |
| 2007/0202462 A1 | 8/2007 | Schwarz et al. |
| 2007/0209947 A1 | 9/2007 | Shrivastava et al. |
| 2007/0256938 A1 | 11/2007 | Fruth |
| 2008/0160259 A1 | 7/2008 | Nielson et al. |
| 2008/0206710 A1 | 8/2008 | Kruth et al. |
| 2008/0210571 A1 | 9/2008 | Comaty et al. |
| 2008/0230397 A1 | 9/2008 | Fecher et al. |
| 2008/0241788 A1 | 10/2008 | Bauer et al. |
| 2008/0241794 A1 | 10/2008 | Urata et al. |
| 2008/0241798 A1 | 10/2008 | Holzner et al. |
| 2009/0068616 A1 | 3/2009 | Uckelmann |
| 2009/0181346 A1 | 7/2009 | Orth |
| 2009/0202378 A1 | 8/2009 | Illston |
| 2009/0275000 A1 | 11/2009 | Jung et al. |
| 2010/0021865 A1 | 1/2010 | Uckelmann et al. |
| 2010/0143868 A1 | 6/2010 | Hintersehr |
| 2010/0152872 A1 | 6/2010 | Dunne et al. |
| 2010/0255441 A1 | 10/2010 | Taormina |
| 2010/0291509 A1 | 11/2010 | Berggren et al. |
| 2010/0310786 A1 | 12/2010 | Dunne |
| 2010/0323327 A1 | 12/2010 | Eriksson et al. |
| 2011/0000076 A1 | 1/2011 | Mcmurtry et al. |
| 2011/0151411 A1 | 6/2011 | Schechner et al. |
| 2011/0170977 A1 | 7/2011 | Vagt et al. |
| 2011/0180971 A1 | 7/2011 | Vagt et al. |
| 2011/0268525 A1 | 11/2011 | Karpowitz et al. |
| 2011/0316178 A1 | 12/2011 | Uckelmann |
| 2012/0148985 A1 | 6/2012 | Jung et al. |
| 2012/0202008 A1 | 8/2012 | Garcia Aparicio et al. |
| 2012/0211155 A1 | 8/2012 | Wehning et al. |
| 2012/0322025 A1 | 12/2012 | Ozawa et al. |
| 2012/0326343 A1 | 12/2012 | Eriksson et al. |
| 2014/0113248 A1 | 4/2014 | Johansson et al. |
| 2015/0093283 A1 | 4/2015 | Miller et al. |
| 2015/0093720 A1 | 4/2015 | Beeby et al. |
| 2015/0273757 A1 | 10/2015 | Pforte et al. |

FOREIGN PATENT DOCUMENTS

| | | | |
|---|---|---|---|
| CN | 1222205 A | 7/1999 | |
| CN | 1620596 A | 5/2005 | |
| CN | 1889898 A | 1/2007 | |
| CN | 101715325 A | 5/2010 | |
| DE | 19533960 A1 | 3/1997 | |
| DE | 102004009127 A1 | 9/2005 | |
| DE | 102008030050 A1 | 8/2009 | |
| DE | 102012108217 A1 | 12/2013 | |
| EP | 1 021 997 A2 | 7/2000 | |
| EP | 1 142 541 A2 | 10/2001 | |
| EP | 1 464 298 A2 | 10/2004 | |
| EP | 1 764 061 A1 | 3/2007 | |
| EP | 1 974 688 A1 | 10/2008 | |
| EP | 2 014 254 A1 | 1/2009 | |
| EP | 2 238 941 A1 | 10/2010 | |
| EP | 2 489 327 A1 | 8/2012 | |
| GB | 1557018 | 12/1979 | |
| GB | 2406534 A * | 4/2005 | ........... B23B 47/288 |
| JP | S54-99739 A | 8/1979 | |
| JP | H02-213500 A | 8/1990 | |
| JP | H3-111042 A | 5/1991 | |
| JP | 2005-515458 A | 5/2005 | |
| JP | 2006-501867 A | 1/2006 | |
| JP | 2007-252897 A | 10/2007 | |
| SE | 1051181 A1 | 5/2012 | |
| SE | 535361 C2 | 7/2012 | |
| WO | 92/22785 A1 | 12/1992 | |
| WO | 02/09612 A1 | 2/2002 | |
| WO | 03/053274 A1 | 7/2003 | |
| WO | 2005/077296 A1 | 8/2005 | |
| WO | 2006/079188 A1 | 8/2006 | |
| WO | 2007/103446 A2 | 9/2007 | |
| WO | 2008/083358 A1 | 7/2008 | |
| WO | 2008/148495 A1 | 12/2008 | |
| WO | 2009/073498 A1 | 6/2009 | |
| WO | 2009/106830 A1 | 9/2009 | |
| WO | 2009/106833 A2 | 9/2009 | |
| WO | 2010/003882 A2 | 1/2010 | |
| WO | 2010/039910 A1 | 4/2010 | |

(56) References Cited

FOREIGN PATENT DOCUMENTS

| WO | 2011/045451 A1 | 4/2011 |
|---|---|---|
| WO | 2011/102118 A1 | 8/2011 |
| WO | 2011/124474 A1 | 10/2011 |
| WO | 2012/064257 A1 | 5/2012 |
| WO | 2012/065936 A1 | 5/2012 |
| WO | 2013/079723 A1 | 6/2013 |
| WO | 2013/167915 A1 | 11/2013 |

OTHER PUBLICATIONS

Jul. 2, 2018 Office Action issued in Chinese Patent Application No. 201380036303.2.
Jun. 12, 2018 Final Decision of Rejection issued in Japanese Patent Application No. 2015-510879.
Jun. 12, 2018 Decision to Decline the Amendment issued in Japanese Patent Application No. 2015-510879.
Jan. 9, 2018 Office Action issued in Japanese Patent Application No. 2015-510878.
Mar. 14, 2018 Office Action issued in Chinese Patent Application No. 201380036083.3.
Jun. 10, 2019 Office Action issued in U.S. Appl. No. 14/399,754.
May 24, 2018 Office Action issued in U.S. Appl. No. 14/399,754.
Nov. 15, 2018 Office Action issued in U.S. Appl. No. 14/399,754.
Braddick, H.J.J. "Mechanical Design of Laboratory Apparatus". Chapman & Hall, London, pp. 5-31, 1960.
Oct. 25, 2012 Search Report and Written Opinion issued in European Patent Application No. 12167523.
Oct. 22, 2012 Search Report issued in European Patent Application No. 12167533.
Oct. 8, 2012 Search Report issued in United Kingdom Application No. 1210121.8.
Jul. 23, 2013 Search Report and Written Opinion issued in International Patent Application No. PCT/GB2013/051210.
Nov. 26, 2012 Search Report issued in European Patent Application No. 12167541.
Oct. 8, 2012 Search Report issued in United Kingdom Application No. 1210120.0.
Aug. 8, 2013 Search Report issued in International Patent Application No. PCT/GB2013/051208.
Jul. 9, 2013 Search Report issued in International Patent Application No. PCT/GB2013/051212.
Dimov, S.S. et al. "Rapid tooling Applications of the selective laser sintering process." Assembly Automation vol. 21, pp. 296-302, 2001.
Kojima M. et al. "Injection mould with permeability utilised Metal Laser Sintering Combined with High Speed Milling." Int. J. Precision Technology, vol. 1, No. 1, 2007, pp. 55-64.
Arrizabalaga, Nicolás Larbáburu. "Máquinas. Prontuario. Técnicas máquinas herramientas." Thomson Editores, 2004, pp. 490.
Gómez. "Procedimientos de Mecanizado." Editorial Paraninfo, 2006, 2nd Edition.
Kalpakjian et al. "Manufactura Ingeniería y tecnología." 4th Edition, 2002.
Teruel. "Control numérico y programación." Ediciones técnicas, 2005.
D T Pham et al. "Selective laser sintering: applications and technological capabilities." Proceedings of the Institution of Mechanical Engineers, vol. 213 Part B, pp. 435-449, 1999.
Kruth, J. P. et al., "Lasers and materials in selective laser sintering." Assembly Automation, vol. 23, No. 4, pp. 357-371, 2003.
Mahbubur et al. "Positioning accuracy improvement in five-axis milling by post processing." Int. J. Mach. Tools Manufact., vol. 37, No. 2, pp. 223-236, 1997.
Gavelis, J. R. et al., "The effect of various finish line preparations on the marginal seal and occlusal seat of full crown preparations." Journal of Prosthetic Dentistry, vol. 92, No. 1, pp. 1-7, Jul. 2004.
Kruth et al. "Rapid Manufacturing of Dental Prostheses by means of Selective Laser Sintering/Melting." Proceedings of the AFPR, 2005.
Shi and Gibson. "Surface Finishing of Selective Laser Sintering Parts with Robot." Solid Freeform Fabrication (SFF) Symposium, Austin TX, 1998, pp. 27-35.
Lai and Gibson. "A Flexible Rapid Prototyping Cell." Solid Freeform Fabrication (SFF) Symposium, Austin TX, 2000, pp. 275-282.
Qu and Stucker. "STL-based Finish Machining of Rapid Manufactured Parts and Tools." Solid Freeform Fabrication (SFF) Symposium, Austin TX, 2001, pp. 304-312.
Extract from a help file from 2004 relating to the Renishaw Productivity + system.
"How to Perfect a Machining Process (or at Least How to Make It More Trustworthy)." Modem Machine Shop, Feb. 4, 2005.
"Under Control" Modern Machine Shop, May 15, 1999.
"Key CNC Concept #4—The Forms of Compensation." Modem Machine Shop, Apr. 1, 1997.
"This Golf Ball Mold is Really Cool." Modem Machine Shop, Sep. 24, 2010.
"[IMTS Preview] AgieCharmilles to Demo Start-to-Finish Manufacturing for Mold Tooling." American Machinist, Aug. 31, 2010.
"GF AgieCharmilles and EOS Partner to Pioneer Toolmaking Process." Prototype Today, 2012.
"Process-Control the Contribution of Touch Trigger Probing." A One-Day seminar relating to Quick Change Tooling for Flexible Machining, Apr. 12, 1989, pp. 1-6.
Buckingham. "Artefact comparison techniques for achieving traceable measurement on CNC machine tools." Industrial Tooling, 1997.
Parker, Richard. "Use of Zirconia in Restorative Dentistry." Dentistry Today, Mar. 2007, pp. 114, 116, 118-119.
"NobelProcera™ Product Overview:Experience the new world of CAD/CAM dentistry." Brochure by Nobel Biocare, 2010, pp. 1-6.
"Solutions for all indications: Tooth- and implant-supported restorations for single teeth to edentulous arches." Brochure by Nobel Biocare, 2010.
"Annual Report 2009: The partner of choice in dentistry." Document by Nobel Biocare, 2009.
Olsson et al."Bridges supported by free-standing implants versus bridges supported by tooth and implant. A five-year prospective study." Pub Med, Jun. 1995.
Shi, Dongping. "Design based integration for improving overall quality of selective laser sintered rapid prototypes." PhD Thesis, Dec. 1999, pp. 1-147.
"Selective Laser Melting Technology Opens Up New Dental and Orthopaedic Applications." 2010, EMDT (European Medical Device Technology) Website.
Kruth J. et al. "Digital manufacturing of biocompatible metal frameworks for complex dental prostheses by means of SLS/SLM." Virtual Modelling and Rapid Manufacturing, Sep. 28-Oct. 1 2005, Portugal, pp. 139-145.
Shi et al. "Improving surface quality of selective laser sintered rapid prototype parts using robotic finishing." Proceedings of the Institution of Mechanical Engineers, Part B: Journal of Engineering Manufacture, http://pib.sagepub.com/content/214/3/197.short.
Stucker et al. "An Integrated Approach to Finish Machining of RP Parts." Solid Freeform Fabrication Symposium Proceedings, Austin TX, Aug. 2002, pp. 594-603.
http://www.cncinformation.com/rapid-prototyping-prototyping-cnc-prototype/rapid-planning-for-cnc-milling-2; Sep. 9, 2014 access date.
Video Clip from http://www.rtbot.net/play.php?id=nP1jUABA6A4 on Oct. 12, 2012. Layer Wise Metal Additive Manufacturing Video.
Video clip from http://www.dentwise.eu/dental/movies/ on Oct. 12, 2012. Dental Wise Video.
U.S. Appl. No. 14/399,754 filed under Beeby, David filed Nov. 7, 2014.
U.S. Appl. No. 14/399,560 filed under Beeby, David filed Nov. 7, 2014.
Aug. 8, 2013 Written Opinion issued in International Patent Application No. PCT/GB2013/051208.
Jul. 9, 2013 Written Opinion issued in International Patent Application No. PCT/GB2013/051212.
Aug. 20, 2015 Office Action issued in Chinese Patent Application No. 201380030706.6.

(56) References Cited

OTHER PUBLICATIONS

Aug. 27, 2015 Office Action issued in Chinese Patent Application No. 201380036083.3.
Oct. 30, 2015 Office Action issued in Chinese Patent Application No. 201380036303.2.
Apr. 8, 2016 Office Action issued in Chinese Patent Application No. 201380036083.3.
May 13, 2016 Office Action issued in Chinese Patent Application No. 201380030706.6.
Aug. 18, 2016 Office Action issued in Chinese Patent Application No. 201380030706.6.
Aug. 26, 2016 Office Action issued in Chinese Patent Application No. 201380036303.2.
Nov. 15, 2016 Office Action issued in European Patent Application No. 13722027.3.
Dec. 8, 2016 Office Action issued in Chinese Patent Application No. 201380036083.3.
Mar. 21, 2017 Office Action issued in Japanese Patent Application No. 2015-510879.
Apr. 28, 2017 Office Action issued in Chinese Patent Application No. 201380036303.2.
Apr. 4, 2017 Office Action issued in Japanese Patent Application No. 2015-510878.
Jul. 6, 2017 Office Action issued in U.S. Appl. No. 14/399,560.
Apr. 25, 2017 Office Action issued in Japanese Patent Application No. 2015-510877.
Jun. 6, 2017 Office Action issued in European Patent Application No. 13 722 029.9.
Jul. 31, 2017 Decision of Rejection issued in Chinese Patent Application No. 201380036083.3.
Aug. 10, 2017 Office Action issued in European Patent Application No. 13 722 027.3.
Aug. 7, 2017 Office Action issued in European Patent Application No. 13722516.5.
Nov. 2, 2017 Office Action issued in U.S. Appl. No. 14/399,754.
Oct. 16, 2017 Office Action issued in Chinese Patent Application No. 201380036303.2.
Dec. 26, 2017 Office Action issued in U.S. Appl. No. 14/399,560.
Nov. 14, 2017 Office Action issued in Japanese Patent Application No. 2015-510879.
"Hole Spacing Jig" <http://lumberjocks.com/topics/19012> (p. 2/4) Post #3 by "GMman", inset diagram.
Aug. 15, 2018 Office Action issued in U.S. Appl. No. 14/399,560.

* cited by examiner

METHOD OF MANUFACTURING AN ARTICLE

This application is a continuation of U.S. application Ser. No. 14/399,672 filed Nov. 7, 2014, which is a § 371 application of PCT/GB2013/051208 filed on May 10, 2013 which is based on and claims priority under 35 U.S.C. § 119 from European Patent Application No. 12167523.5 filed on May 10, 2012. The contents of each of the above applications are incorporated herein by reference.

TECHNICAL FIELD

This invention relates to a method for manufacturing an article, for example an article comprising at least one dental restoration.

BACKGROUND

Rapid manufacturing techniques are becoming more widely used to produce a wide variety of parts. In particular, techniques which build parts layer-by-layer are becoming more well known and used in industry to manufacture custom parts. Selective laser sintering is one such rapid manufacturing technique whereby products can be built up from powdered material, such as powdered metal, layer-by-layer. For example, a layer of powdered material can be applied to a bed of the laser sintering machine and a laser is then controlled so as to sinter or melt select parts of the powdered material so as to form a first layer of the part. Another layer of powder is then applied on top and the laser is again controlled to sinter or melt another layer of the part. This process is repeated until the whole part is formed. The formed part is then removed from the bed of powder. Such techniques are well known and for instance described in EP1021997 and EP1464298.

Compared to more traditional techniques such as milling parts from billets or blanks, such techniques offer rapid manufacturing, as well as facilitate manufacturing of complex parts and can help to minimise material wastage. As a result it is becoming more desirable to manufacture parts using such techniques. Indeed, it is known to use such a technique for forming dental restorations, and in particular dental frameworks, which are typically complex bespoke parts.

However, products made by such a technique sometimes need a further operation in order to alter the surface finish, and/or the precision of certain features on the part, which cannot be achieved via the rapid manufacturing technique alone.

SUMMARY

According to a first aspect of the invention there is provided a method of manufacturing an article, comprising: taking an article formed in an initial state via an additive manufacturing process; performing a second manufacturing process to transform the article into a second state, which comprises mounting the article in a holding device, processing at least one first feature on the article, and processing at least one mounting feature on the article (for example processing at least one set of mounting features on the article), re-mounting the article via the at least one mounting feature (e.g. via the at least one set of mounting features), and then processing at least one second feature on the article.

Accordingly, the additive manufacturing process could have been used to form the bulk of the article and the second manufacturing process could be used to finish off certain aspects or features of the article. It can in some situations be necessary to re-mount/re-orient the article during the second manufacturing process to enable different features to be processed. This is particularly the case where the machine performing the second manufacturing process does not facilitate rotation of the article and/or device processing the article, and/or where the article is large with respect to the machine such that it is difficult or not possible to rotate the article. However, such re-mounting/re-orientation can lead to inaccuracies in the processing of features. For example, when machining the at least first and at least second features, it can be important to maintain a level of accuracy in their relative position. Re-mounting/re-orientation of the article between the machining of the at least first and at least second features can introduce a source of error.

However, such errors can be reduced by performing the method of the invention because the method comprises processing at least one mounting feature (e.g. at least one set of mounting features) as well as the at least one feature, and then the at least one second feature on the article is processed whilst the article is mounted using said processed at least one (e.g. set of) mounting feature(s). As the position of the at least one (e.g. set of) mounting feature(s) can be controlled by the second manufacturing process, its (or their) position with respect to the at least one first feature can be constrained in a known manner. Hence, when the article is re-mounted using the at least one (e.g. set of) mounting feature(s), the position of the article and hence the at least one first feature can be known because they are controlled/constrained by the at least one (e.g. set of) mounting feature(s). It is therefore possible to accurately control the position at which the at least one second feature is processed with respect to the at least one first feature. As will be understood, the degree to which the position of the first features is known within the machine's operating volume when it is mounted via the at least one (set of) mounting feature(s), depends on various factors including the accuracy of the machining process. However, what can be important is that the degree is known and/or is within a required (e.g. predetermined) tolerance, which can for example be within a position tolerance diameter of 100 μm (microns), and for instance within a position tolerance diameter of 50 μm (microns).

Accordingly, the present invention enables the part to be mounted in a plurality of different orientations and means that different sides of the article can easily be processed, even by a tool approaching that article from the same orientation. As a result, it can reduce the complexity of the machinery required for processing the article. For example, it can mean that the article can be processed using machinery with limited rotational degrees of freedom, and indeed can obviate the need for any rotational degrees of freedom. Not only can this reduce the cost of the machinery involved, the potential size of the machinery involved, but it can also mean that any imprecision introduced by the rotational axes can be reduced or completely avoided. Indeed, it can mean that the machinery used for performing the second processing operation can simply be a 3 linear axis machine.

Accordingly, the at least one (set of) mounting feature(s) can define the position of the article within the machine operating volume so as to obviate the need to probe the article to determine its location prior to operating on the article after said re-mounting. The at least one (set of) mounting feature(s) can ensure that the position and orientation of the article is known when it is re-mounted in the machine tool. In particular, it can ensure that the lateral position in three orthogonal degrees of freedom, and the rotational orientation about three orthogonal rotation axes is constrained in a known way. Accordingly, the at least one (set of) mounting feature(s) could be described as being location defining mounting features. This can mean that operation on the article by the machine to process the at least one second feature can take place straight away without time consuming position and/or orientation identification operations which require inspection of the location of the article, e.g. without probing the article to find its location. Accordingly, optionally the position of at least a part of the article (e.g. at least the position of the at least one first feature) once it has been re-mounted via the at least one (set of) mounting feature(s), can be determined from knowledge of the position of the at least one (set of) mounting feature(s).

Accordingly, the tool (e.g. the machine tool) performing the second manufacturing process could determine the position of at least a part of the article based on the knowledge of the position of the at least one (set of) mounting feature(s) and other data concerning the article. The other data could comprise data concerning the position of the at least one first feature. The other data could comprise data concerning the position of other features of the article.

Accordingly, in line with the above, the at least one (set of) mounting feature(s) could be configured such that the position and orientation of at least a part of the article in all three linear and three rotational degrees of freedom within the machine operating volume is known and defined by virtue of the interaction of the mounting features with the holding device. For example, the mounting features can be kinematic mounting features. As will be understood, and as for instance described in H. J. J. Braddick, "Mechanical Design of Laboratory Apparatus", Chapman & Hall, London, 1960, pages 11-30, kinematic design involves constraining the degrees of freedom of motion of a body or feature using the minimum number of constraints and in particular involves avoiding over constraining. This ensures highly repeatable positioning of the article with respect to the holding device, and means that the article will sit on the holding device in a predictable known manner. Accordingly, such kinematic mount features could engage with corresponding kinematic mount features on the holding device of the tool (e.g. machine tool) which is to perform the second manufacturing process.

The article can also comprise gross orientation features which restrict the gross orientation that the user can place the article on the holding device. These could be processed prior to said re-mounting. In particular, preferably they are configured such that they enable the article to be placed in one orientation only on the holding device. Such a feature could be provided by the at least one (set of) mounting feature(s). Optionally, they are provided as separate features to the (set of) mounting feature(s). Preferably, such gross orientation features do not interfere with the control of the position and orientation of the article provided by the engagement of the (set of) mounting feature(s) on the article with corresponding features on the holding device.

The at least one second feature on the article could be located on a substantially opposite side of the article to the at least one first feature.

Re-mounting/reorienting the article via the at least one mounting feature can comprise turning the article over. The method could comprise re-mounting the article such that at least part of the machining volume within which the second features are processed overlaps with the machining volume within which the first features are processed. In other words, the article can occupy substantially the same volume of the machine tool apparatus that processes the article when the article is mounted during the processing of the at least one first feature and at least one (e.g. set of) mounting feature(s) and when the article is mounted during the processing of the at least second feature. In particular, the volume occupied by the article (and in particular for example the volume occupied by the at least one product of the article) when mounted during the processing of the at least one first feature and at least one (e.g. set of) mounting feature(s) can substantially overlap with the volume occupied by the article (and in particular for example the volume occupied by the at least one product of the article) when the article is mounted during the processing of the at least second feature, e.g. by at least 50%, more preferably by at least 75%, especially preferably by at least 85%. This can reduce the volume of the machine performing the processing that needs calibrating or an error map generating for.

The article could have been built via the additive manufacturing process according to a computer model e.g. a CAD model, of the article.

The second manufacturing process could comprise determining the location of features of the article using data concerning the position of such features. Such data could be derived from the computer model. Accordingly, the method can comprise receiving data concerning the position of at least some features of the article.

The article could have been built layer-by-layer via the additive manufacturing process. The article could have been built via a laser consolidation process, such as a laser sintering or melting process, also known as selective laser sintering or selective laser melting. Optionally, the article could have been built via a laser cladding process, a fused deposition modelling (FDM) process or an e-beam melting process. The method can comprise the step of forming the article via the additive process.

The second manufacturing process can comprise a subtractive process. Accordingly, processing the at least one first feature, at least one second feature and/or the at least one set of mounting features can comprise removing material from the article. For example the second manufacturing process can comprise a machining process, for example a milling process. Accordingly, the method can comprise mounting the article in a machine tool in a plurality of different orientations, and machining the article in said plurality of different orientations.

The at least one (set of) mounting feature(s) can have already been at least partially formed in the article via the additive manufacturing process. Accordingly, processing the at least one (set of) mounting feature(s) can comprise finishing the (set of) mounting feature(s). This could comprise removing material on the at least one (set of) mounting feature(s). It might be that the at least one (set of) mounting feature(s) are formed entirely during the second manufacturing process.

It might be that the at least one first feature and/or the at least one second feature is formed entirely during the second manufacturing process. Optionally, the at least one first feature and/or the at least one second feature can have already been at least partially formed in the article via the additive manufacturing process. Accordingly, processing the at least one first feature and/or the at least one second feature can comprise finishing the at least one first feature and/or the at least one second feature. This could comprise removing material on the at least one first feature and/or the at least one second feature. Accordingly, the at least one first feature and/or the at least one second feature could be provided with excess material which is removed during the second manufacturing process. Accordingly, when the method comprises forming the article via the additive processes, this step can comprise adding excess material onto at least the at least one first feature and/or the at least one second feature. Such excess material can be material in excess to what is ultimately desired for the finished product.

The article can comprise at least one dental restoration. The article could comprise at least one implant supported dental restoration. The dental restoration could be a bridge. The dental restoration could be a single tooth restoration, such as an implant supported abutment or crown. Other material could be added to the dental restoration, to finish the restoration. For instance, porcelain or a crown could be added to provide a finish that is more aesthetically similar to natural teeth.

The at least one first feature and/or the at least one second feature can a part of the dental restoration that is to interface with another object. Such features can require a good fit with the other object. Ensuring a good fit can be important for many reasons, e.g. structurally so as to reduce the chance of failure of the dental restoration. It can also be important to ensure a good fit so as to avoid gaps which could harbour bacteria. For instance, the method can comprise machining a region that is to interface with a tooth prepared for receiving the restoration, commonly known as a "prep" in a patient's mouth, or an implant in a patient's jaw.

The article can comprise a plurality of products joined together. As will be understood, the products can be subsequently separated from each other. Accordingly, a plurality of products can be formed and processed concurrently. As they are joined together, they can be transported together and mounted together in a machine for performing the second manufacturing process.

The article can comprise at least one product and at least one member on which the at least one (set of) mounting feature(s) are provided. Accordingly, the mounting features can be provided separate from the product(s). As will be understood, the at least one member can be subsequently separated from the product subsequent to all processing requiring the member. The member could be a holding member (e.g. a clamp member) via which the article can be held (e.g. clamped) to define and maintain its location during the second manufacturing process. Preferably any preformed (set of) initial mounting feature(s) are also formed on the member. The at least one member may comprise a central hub around which the at least one product is arranged.

The plurality of products can be joined together via the at least one member.

The plurality of products can comprise a plurality of dental restorations. For instance, the plurality of products can comprise a plurality of dental abutments.

The article formed in an initial state via the additive manufacturing process could comprise at least one preformed (set of) initial mounting feature(s) (i.e. a different (set of) feature(s) to that already mentioned). The second manufacturing process could comprise mounting the article in a holding device, via the pre-formed (set of) initial mounting feature(s). The second manufacturing process can then comprise processing said at least one first feature and at least one (set of) mounting feature(s) on the article.

As with the above described at least one (set of) mounting feature(s), the pre-formed (set of) initial mounting feature(s) can be configured to define the position of the article within the machine operating volume so as to obviate the need to probe the article to determine its location prior to operating on the article. The features mentioned above in connection with the at least one set of mounting features also apply to this pre-formed (set of) initial mounting feature(s).

There can be two main sources of error in the position of the at least one feature (e.g. said at least one first feature) to be processed. One source of error can be the uncertainty in the position of the at least one feature to be machined relative to the pre-formed (e.g. set of) initial mounting feature(s) (and hence relative to the holding device of the machine). This error can be dependent on the accuracy of the additive manufacturing process. Accordingly, such errors can vary depending on the accuracy of the additive manufacturing process, but typically are known and can be defined with respect to the process used. Another source of error can be the position repeatability of the article with the holding device of the machine (which can be dictated by the configuration of the pre-formed (e.g. set of) initial mounting feature(s) and corresponding features on the holding device). Preferably, the pre-formed (e.g. set of) initial mounting feature(s) is configured such that the ratio of i) uncertainty of the position of the part (e.g. said at least one first feature to be machined) to ii) the position repeatability of the article is not more than 50:1, more preferably not more than 10:1, especially preferably not more than 5:1, for example not more than 4:1, for instance not more than 1:2. As will be understood, the uncertainty of the position of the part and the position repeatability of the article can be measured as position tolerance diameters.

Accordingly, preferably the method is configured, and for example the pre-formed (e.g. set of) initial mounting feature(s) of the article and the holding device are configured, such that when the article is mounted in the holding device, the location of the at least one first feature to be processed within the machine's operating volume is known to within a required, e.g. predetermined, tolerance, and for example to within a position tolerance diameter of 100 μm (microns), more preferably to within a position tolerance diameter of 50 μm (microns).

Optionally, the at least one (set of) mounting feature(s) can be formed on an opposite side of the article to the pre-formed (set of) initial mounting feature(s). This can be such that the article can be processed on first and second opposite sides by mounting the article via the pre-formed (set of) initial mounting feature(s) and then via the at least one (set of) mounting feature(s). Accordingly, the method can comprise turning the article over so as to then mount it onto its at least one (set of) mounting feature(s).

The article can be re-mounted via its at least one (set of) mounting feature(s) onto the same holding device that was used to mount the article via its pre-formed (set of) initial mounting feature(s). More particularly, the holding device can have a (set of) feature(s) which is(are) configured to mate with the pre-formed (set of) initial mounting feature(s) and the at least one (set of) mounting feature(s) on the article to hold and define the location of the article during the second manufacturing process. The article can be re-mounted via its at least one (set of) mounting feature(s) onto the same (set of) feature(s) of the holding device that was used to mount the article via its first (set of) mounting feature(s). Accordingly, the pre-formed (set of) initial mounting feature(s) and the at least one (set of) mounting feature(s) can be identical.

As mentioned above, the at least one (set of) mounting feature(s), and the at least one pre-formed (set of) initial mounting feature(s) can be provided on substantially opposing faces of the article. The at least one (set of) mounting feature(s), and the at least one pre-formed (set of) initial mounting feature(s) can be configured such that at least part of the machining volume in which the second features are processed overlaps with the machining volume in which the first features are processed. Accordingly, the different (sets of) mounting feature(s) can be arranged such that the substantially the same volume of machine is used when mounted using each (set of) mounting feature(s). In other words, the at least one pre-formed set of initial mounting features and the at least one set of mounting features can be configured such that the article occupies substantially the same volume of the machine tool apparatus that processes the article when the article is mounted in the holding device via the at least one pre-formed set of initial mounting features and the at least one set of mounting features. In particular, the volume occupied by the article (and in particular for example the volume occupied by the at least one product of the article) when mounted via the at least one pre-formed set of initial mounting features can substantially overlap with the volume occupied by the article (and in particular for example the volume occupied by the at least one product of the article) when mounted via the at least one set of mounting features, e.g. by at least 50%, more preferably by at least 75%, especially preferably by at least 85%. This can reduce the volume of the machine performing the processing that needs calibrating or an error map generating for.

According to another aspect of the invention, there is provided an article made by an additive manufacturing process comprising at least one mounting feature formed subsequent to the additive manufacturing process by a second manufacturing process different from the additive manufacturing process.

According to another aspect of the invention, there is provided a product or article produced by a method described herein.

According to another aspect of the invention, there is provided a method of manufacturing a dental restoration comprising: i) forming a dental restoration body in an initial state via an additive process, the dental restoration body comprising a mount having at least one set of location features; ii) mounting the dental restoration body in its initial state into a machine tool via the mount's at least one set of location features; and iii) machining the dental restoration body from both substantially opposing first and second sides of the dental restoration body to transform the dental restoration body into a secondary state.

Accordingly, the method of the invention utilises different manufacturing techniques at different stages to form an accurate dental restoration in an efficient manner.

The use of an additive process can be advantageous over machining the entire dental restoration body from a solid blank as it requires significantly less material and also can be less time consuming. It also allows the formation of a geometry that would be impossible with machining processes alone.

The provision of the location features can remove the need for probing to ascertain the dental restoration body's position within the machine tool. The location features can ensure that the location of the dental restoration body is known when it is mounted in the machine tool.

Step iii) can comprise machining the dental restoration body from the first side of the dental restoration body, re-orienting the initial state dental restoration, and then machining the dental restoration body from the second side of the initial state dental restoration body.

The dental restoration body in its initial state can comprise at least two sets of location features. The dental restoration body can be mounted in the machine tool via a first set of location features during machining from its first side, and via at least a second set of location features during machining from its second side.

The at least second set of location features can at least partly be machined during said machining from the first side of the dental restoration body.

The at least second set of location features can at least partly be formed during the additive process. Accordingly, the at least second set of location features can be machined to provide the final formation of the at least second set of location features.

The dental restoration body can be mounted in the machine tool via its first and at least second set of location features onto the same set of machine tool mounting features.

The at least one set of location features can comprise at least one set of kinematic mounting features.

The dental restoration body can comprise at least one interface for interfacing with an implant in a patient's jaw (so as to locate the dental restoration in the patent's jaw) which is presented on one of said first and second sides of the dental restoration.

It can be important that the at least one interface (the area(s) of the dental restoration body which mate with the implant(s) in the patient's jaw) has a very precise finish. Without such a precise finish, the fit between the interface(s) and implant(s) could be inadequate and which can lead to the dental restoration being inadequately secured within the patient's jaw.

Accordingly, in the dental restoration body's initial state, the at least one interface can be formed with an excess of required material. The method can further comprise machining said at least one interface to remove at least some of said excess material.

A plurality of interfaces, spaced along the dental restoration body can be provided. This is especially the case when the dental restoration is a bridge. It has been found that if the plurality of interfaces are not accurately formed, for example if the spacing between the interfaces differs from the spacing between the corresponding mounts in the patient's jaw, then the dental restoration body can become contorted when fixed into position. This contortion can leads stresses in the dental restoration body, which in turn can lead to undesired stresses on the implants. Such stress on the implants can cause discomfort for the wearer and a tendency for the dental restoration body to work itself loose or even fail Accordingly, the method can comprise machining at least one of said plurality of implant interfaces so as to remove excess material, thereby manipulating the relative position of said plurality of implant interfaces relative to each other.

The at least one implant interface can be provided on the first side of the dental restoration body.

The at least one interface can be an implant interface for interfacing with an implant secured into a patient's jaw.

The dental restoration body in its initial state can comprise at least one bore for receiving a fastener for securing the dental restoration body to an implant in a patient's jaw. As will be understood, the surface against which the head of a fastener abuts the dental restoration body can require a high level of smoothness in order to ensure a secure fit. The method can therefore comprise machining said at least one bore so as to provide a final formation of said at least one bore.

The machining of said at least one bore can be performed from said second side of the dental restoration body.

An additive process can comprise a selective laser melting/sintering process.

The dental restoration can be a bridge. The dental restoration can be an implant supported bridge.

The dental restoration body can form the final outer shape of the dental restoration. Optionally, the dental restoration body can be a framework onto which an outer structure can be formed to provide the final outer shape of the dental restoration. Accordingly, the method can comprise adding an outer structure onto the framework. The outer structure can comprise a layer of porcelain.

This application describes a method of manufacturing an article, comprising: forming an article in an initial state using a first manufacturing process (e.g. an additive manufacturing process) which builds the article layer-by-layer, including forming at least one first (e.g. a first set of) mounting feature(s); performing a second manufacturing process to transform the article into a second state, which comprises mounting the article in a holding device via the at least one first (e.g. a first set of) mounting feature(s), processing at least one feature on the article, and processing (e.g. forming or finishing) at least a second (e.g a second set of) mounting feature(s) on the article, re-mounting the article via the at least second (e.g. second set of) mounting feature(s) and processing another feature on the article.

Accordingly, the additive manufacturing process could be used to form the bulk of the article and the second manufacturing process could be used to finish off certain aspects or features of the article. The use of at least first and second (e.g. first and second sets of) mounting feature(s) enables the part to be mounted in a plurality of different orientations and can mean for example that different sides of the article can easily be processed, even by a tool approaching that article from the same orientation. As a result, it can reduce the complexity of the machinery required for processing the article. For example, it can mean that the article can be processed using machinery with limited rotational degrees of freedom, and indeed can obviate the need for any rotational degrees of freedom. Not only can this reduce the cost of the machinery involved, the potential size of the machinery involved, but it can also mean that any imprecision introduced by the rotational axes can be reduced or completely avoided. Indeed, it can mean that the machinery used for performing the second processing operation can simply be a three linear axis machine.

The provision of the mounting features on the article can reduce or remove the need for probing to ascertain the dental restoration body's position within the machine tool. The mounting features can ensure that the location of the article is known when it is mounted in the machine tool. Accordingly, the mounting features could be described as being location defining mounting features. As will be understood, location can include the position and orientation of the artefact.

Furthermore, processing the at least second (e.g. second set of) mounting feature(s) (which are used to re-mount the article in a second position and/or orientation) means that the precision of the location of the feature processed when mounted using the at least second set of features, with respect to those features processed when mounted using the first (e.g. first set of) mounting feature(s), is dictated by the precision of the second process machine forming the at least second (e.g. second set of) mounting feature(s) and not the precision of the first process.

This application also describes a method of manufacturing a dental implant-supported abutment comprising: building an abutment, including the part for interfacing with an implant member, from a powdered material, layer-by-layer, via a laser sintering process. Such a method can comprise processing at least a part of the abutment subsequent to said laser sintering process.

Said processing can comprise removing material from the abutment, e.g. via machining. The method can comprise processing the part for interfacing with an implant member. Processing can comprise, subsequent to said laser sintering process, mounting the abutment in a device for holding the abutment during said processing. The laser sintering process can comprise building a mount connected to the abutment via which the abutment is mounted in the device for holding the abutment during said processing. Preferably, the abutment and mount are configured such that when the abutment is mounted in the device for holding the abutment during said processing, the abutment's longitudinal axis, which could for example be parallel or even coincident with the axis of any current or yet to be formed bore of the abutment (through which an implant screw, or screwdriver for fastening an implant screw can be received), and optionally for example the axis of the part for interfacing with the implant member is parallel to the tool, e.g. cutting tool, for processing the abutment. The laser sintering process can comprise building a plurality of abutments connected to the same mount. At least two, and preferably all, of the plurality of abutments can be oriented such that their part for interfacing with an implant member are oriented in the same direction, e.g. such that their longitudinal axes are parallel to each other.

DETAILED DESCRIPTION

The below description provides an example of how the invention can be used to manufacture an implant-supported bridge. As will be understood, an implant-supported bridge is a particular type of dental restoration which in use is secured to a plurality of dental implants already implanted into a patient's jaw so as to retain the dental restoration in the patient's mouth. Typically, implant-supported bridges are used to replace a plurality of teeth. Implant-supported bridges are typically made from a base structure of metal, with porcelain being added to the bridge's base structure before its fitting to provide the desired finish form and look of the bridge. The bridge's base structure is often termed a "framework" or "superstructure".

Figure 10A:
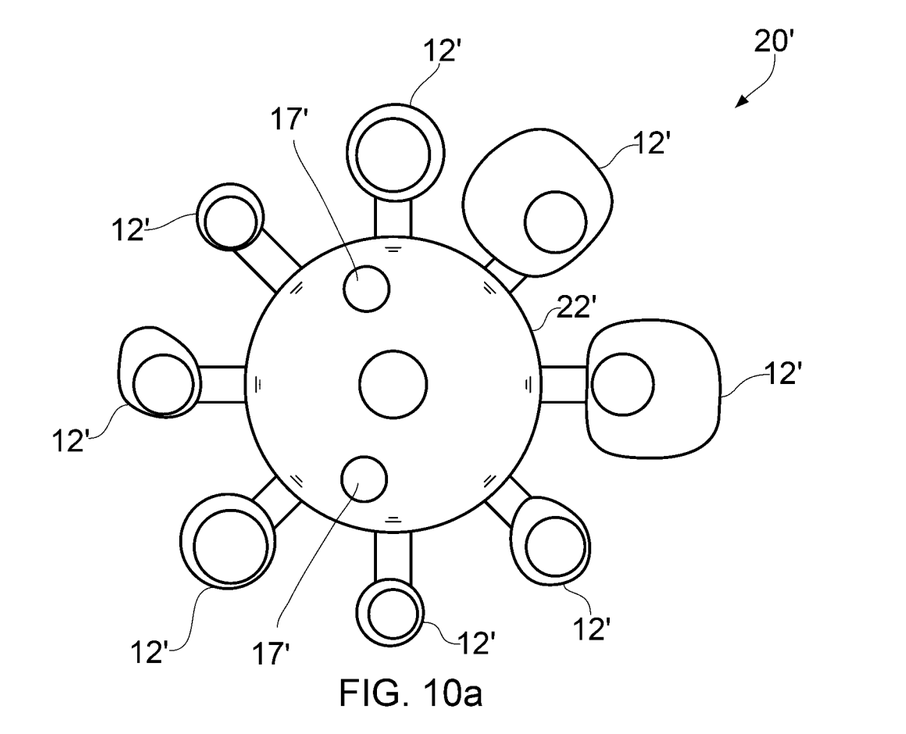
FIGS. 10a and 10b show schematically underside views of an article comprising a plurality of abutments connected to a central hub in its initial state.
Figure 10B:
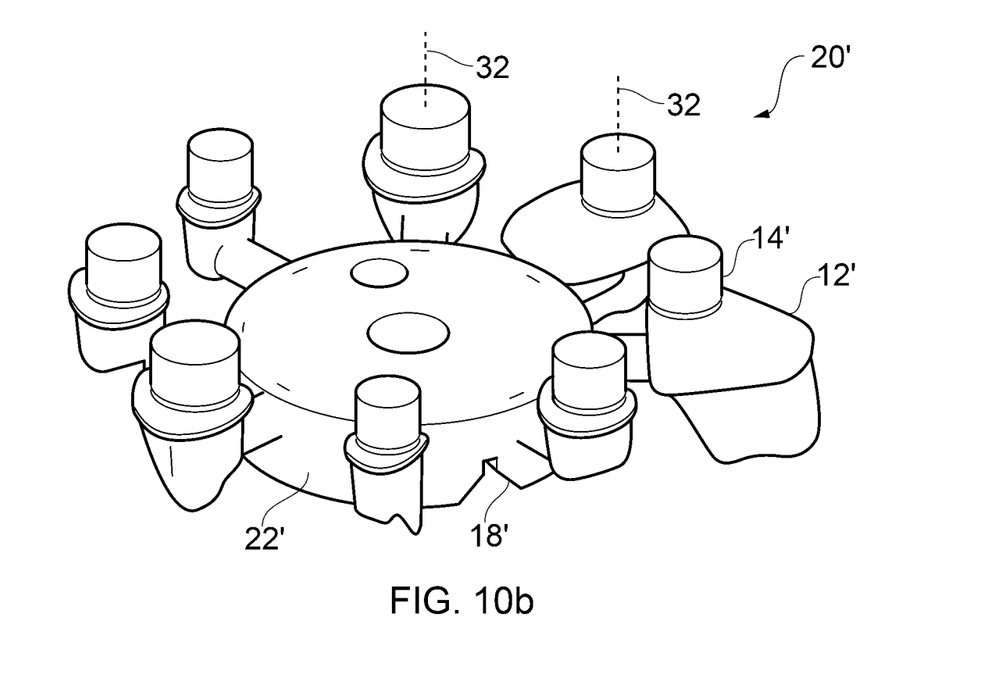
Figure 11A:
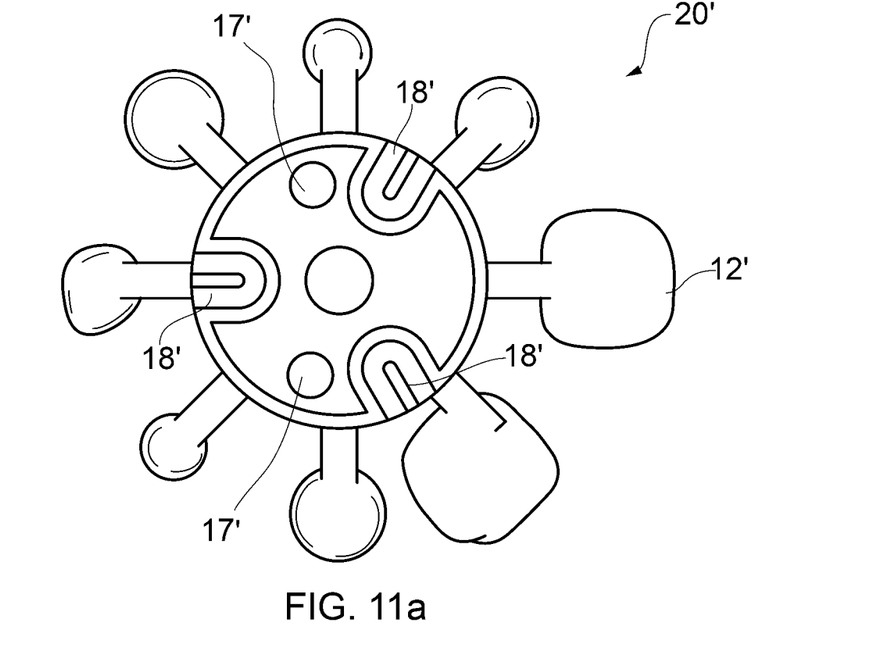
FIGS. 11a and 11b show schematically top-side views of the article shown in FIG. 10.
Figure 11B:
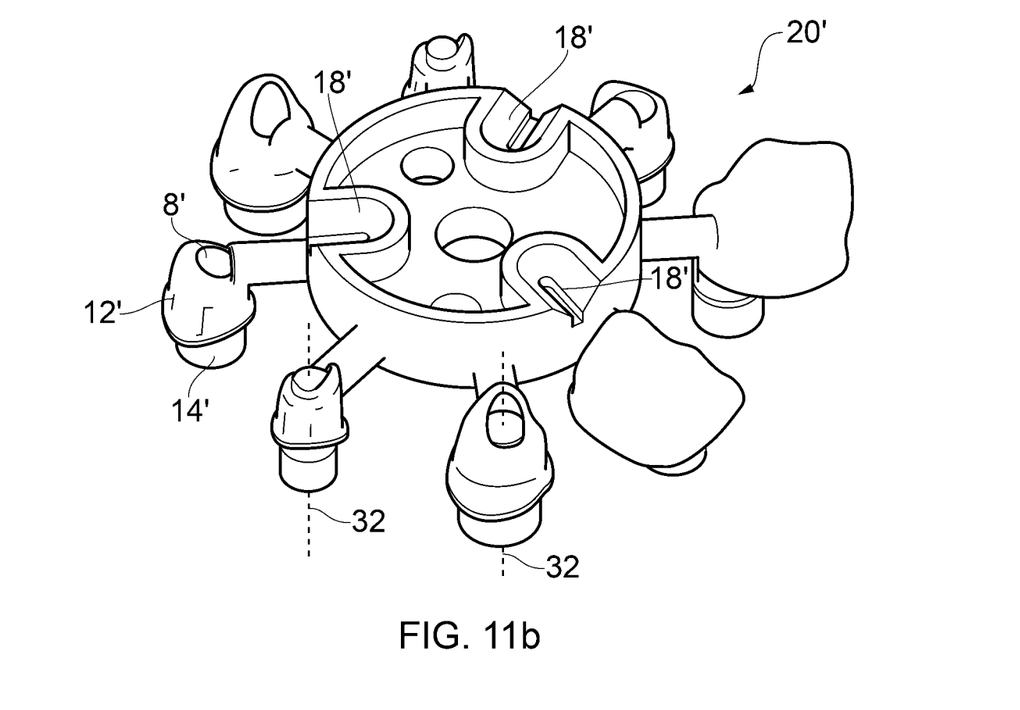

As will be understood, the invention is not limited to the manufacture of implant-supported bridges, but could also be used for instance in the manufacture of other types of dental restorations, such as single tooth restorations, for example implant-supported abutments (as illustrated in FIGS. 10a, 10b, 11 a and 11b), or crowns. However, the invention is also not limited to dental restorations in general. Rather, the invention can be used in the manufacture of a wide range of different types of products, such as other types of medical implants, aerospace parts and jewellery.

As will be understood, an implant supported bridge needs to be made accurately so as to ensure that the bridge provides a comfortable and enduring fit in a patient's mouth. It is known to use a machine tool, such as a CNC milling machine to produce a dental bridge's framework from a blank of sufficient volume so that the entire framework can be machined in one piece. As will be understood, for implant-supported bridges, the blank is typically a solid piece of metal, for example titanium or a cobalt chrome alloy. Other materials can be used, for instance zirconia, although in this case, a metal link member is sometimes required between the zirconia body and implant. In any case, such a milling/machining technique results in a highly accurate framework being formed, but is time consuming, expensive and involves significant material wastage The embodiment described according to the present invention makes use of an additive process to produce an initial form of the bridge's framework, and then a subtractive process for finishing the framework, e.g. to improve surface finish and/or the precision of certain features. For example, as explained in more detail below a machining process is used to finish at least selective parts of the first and second sides of the dental restoration body to a high degree of accuracy. The use of an additive process can be advantageous over machining the entire dental restoration body from a solid blank as it requires significantly less material and also can be less time consuming.

Figure 1:
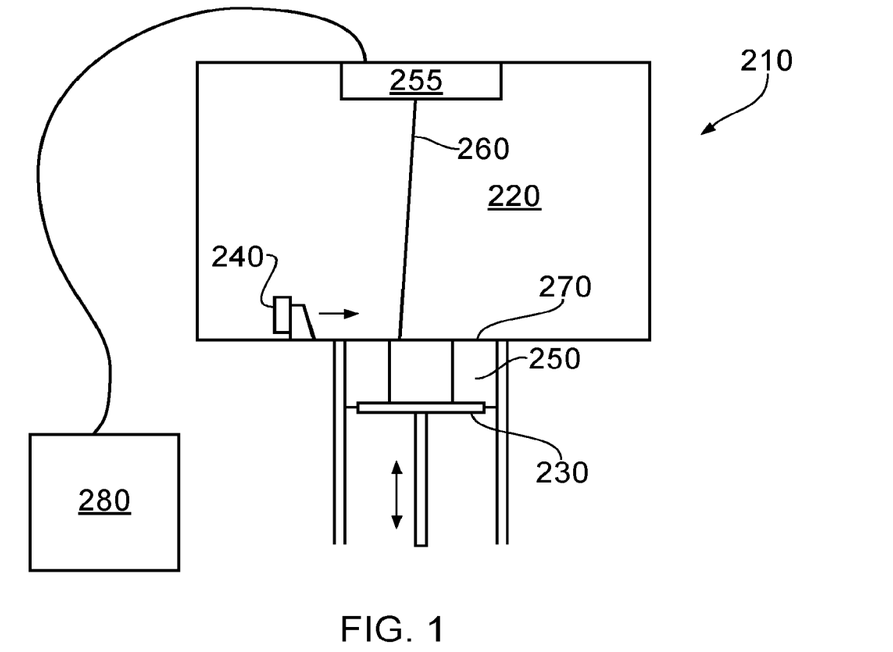
FIG. 1 shows schematically a selective laser sintering machine for forming an article.

FIG. 1 illustrates a typical arrangement of a build chamber 210 of a selective laser sintering/melting machine. The build chamber 210 defines a space 220 above a lowerable build platform 230. The build chamber 220 comprises a powder dispensing and coating apparatus 240 for spreading powder 250 over the surface of the build platform 230. A window 255 in an upper wall of the chamber 210 allows a laser beam 260 to be directed to irradiate powder spread at a build surface 270, so as to selectively sinter/melt the powder thereby forming a layer of the article 20. The laser and lowerable platform 230 can be controlled by a controller, 280, such as a PC, which has a program defining the process for forming the article 20. The program can control the laser sintering process on the basis of CAD data of the part to be formed. In particular, the CAD data can be split into a number of layers, each layer corresponding to a layer to be formed by the laser sintering process.

Figure 2:
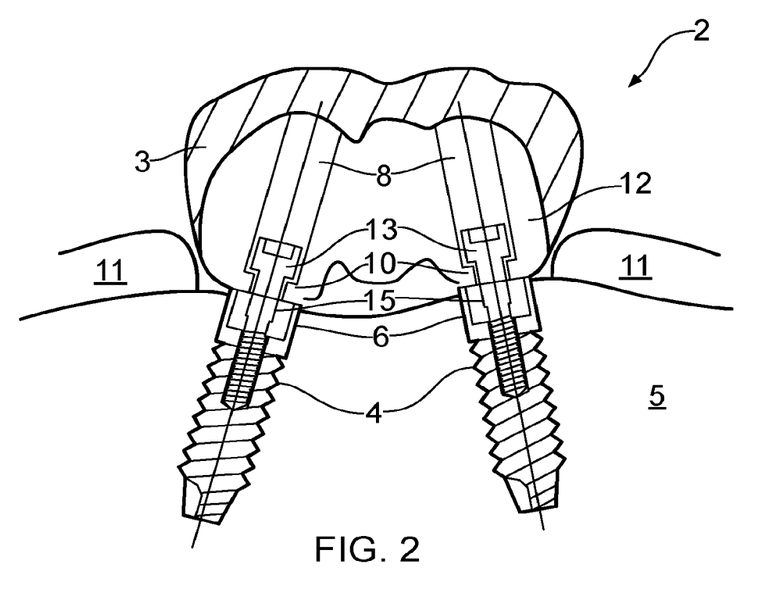
FIG. 2 shows schematically a cross-sectional front view of a bridge attached to supporting implants.

FIG. 2 illustrates how a completed dental restoration, in this case a bridge 2, in its final state may be affixed to implants 4 in a patient's jaw 5. As shown, the bridge 2 crosses the gums 11 or gingiva. As shown, the bridge 2 comprises a framework 12 onto which an outer layer of porcelain 3 is added to provide the final outer shape of the dental restoration. FIG. 2 shows the implant/framework interface 6, which is the region at which the framework 12 and the implant 4 engage each other. This is a portion of the framework's 12 surface that is to be finished to a high degree of accuracy. As shown, the bridge 2 comprises a series of counter bores 8 formed in the bridge framework 12 into which implant screws can be located. The counter bores 8 comprise an upper section 13 and lower section 15. The lower section 15 has a smaller radius than the upper section 13, and in particular has a radius smaller than the head of the screw 10 which is used to secure the bridge 2 to the implants 4. As shown, when screwed into the implants 4 through the counter bores 8, the screws 10 securely fasten the counter bores 8, and hence the bridge 2, to the implants 4.

Figure 3:
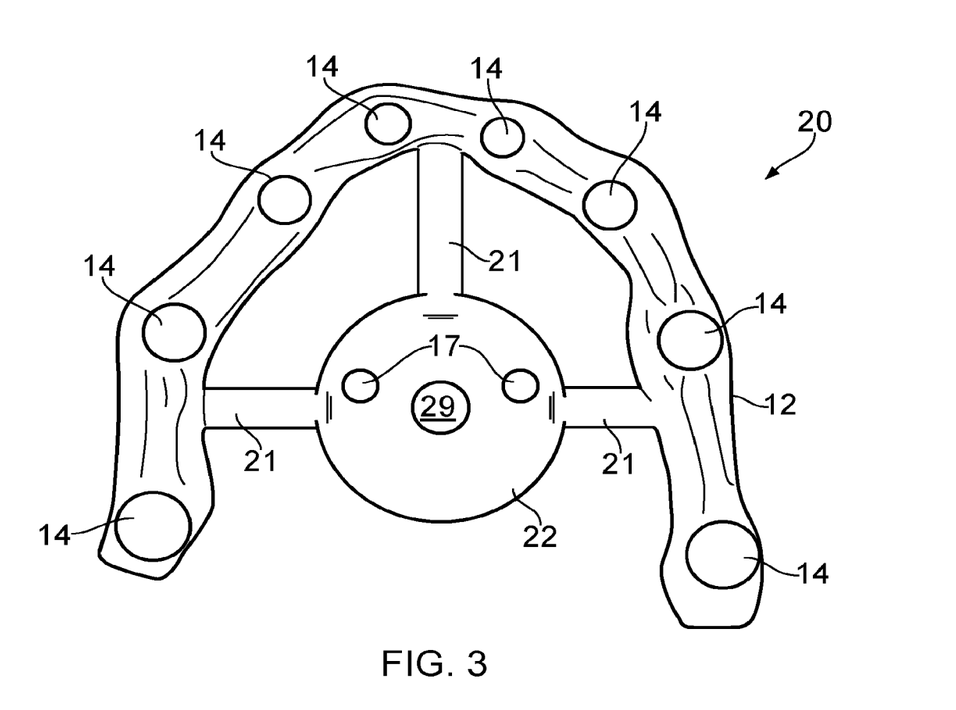
FIG. 3 shows schematically an underside view of a bridge framework in its initial state.
Figure 4:
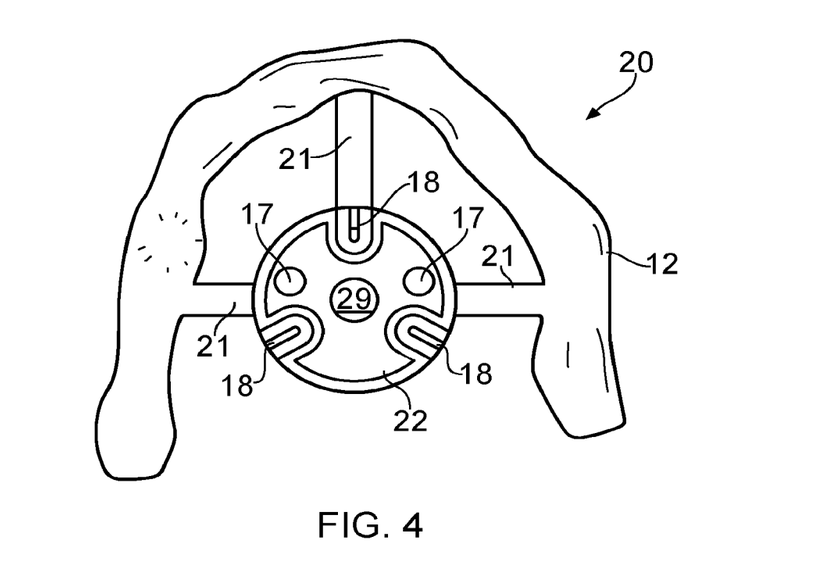
FIG. 4 shows schematically a top-side view of a bridge framework in its initial state.

FIGS. 3 and 4 respectively show underside and topside views of an article 20 comprising the bridge framework 12 in its initial state produced according to the method of the invention. The lowermost surface of the framework 12 comprises circular disk/boss-like protrusions of excess material 14 from which the framework's 12 implant interfaces are to be machined. The article 20 also comprises a location hub 22, which comprises three v-groove features 18 defining a first kinematic mount upon its top surface. As described below, the three v-groove features 18 are used to accurately locate the article 20 and hence the bridge framework 12 in a known position and orientation in the machine tool apparatus' volume via the machine tool clamp 25 (described in more detail below). As also shown, the location hub 22 also comprises two orientation bores 17 extending all the way though the location hub 22. As described below, these bores 17 can be used to ensure the correct orientation of the bridge framework 12 in the machine tool clamp 25. The location hub 22 is situated on the inside of the bridge framework 12 arch, with the location hub 22 and the bridge framework 12 attached by three approximately cylindrical connectors 21.

Figure 5:
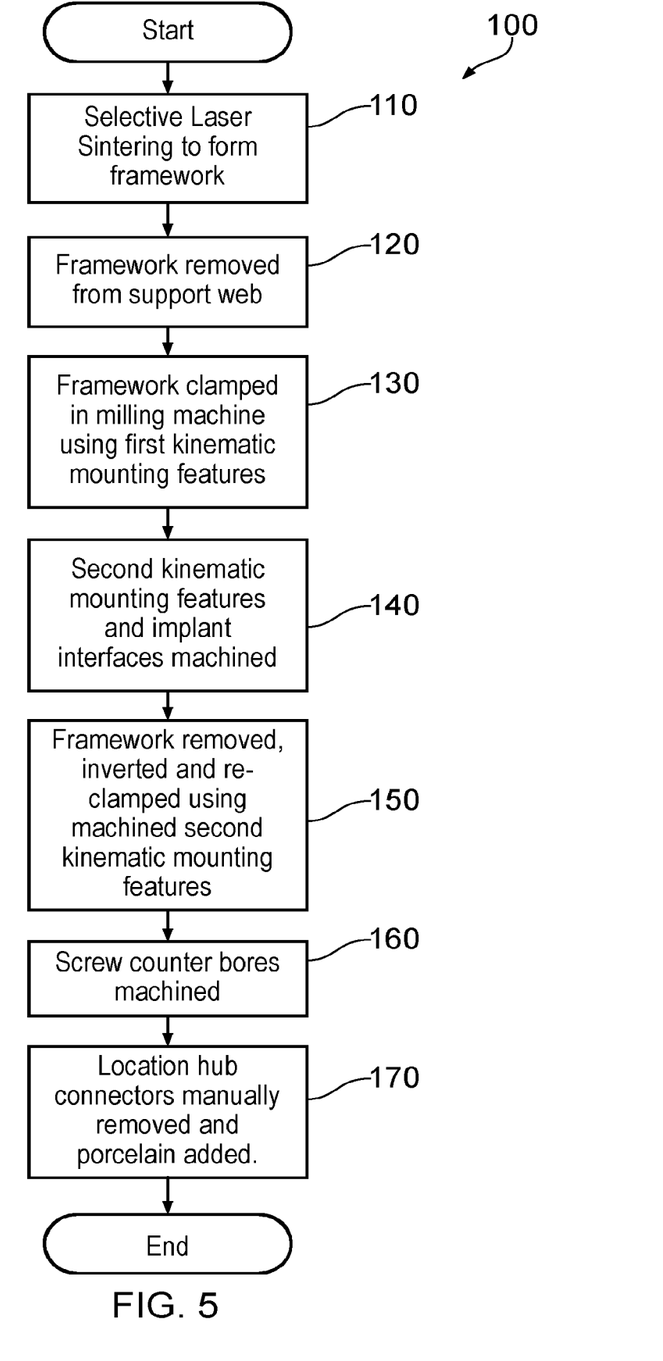
FIG. 5 is a flowchart illustrating a method according to the invention.

FIG. 5 is a flowchart illustrating the method of producing an implant-supported bridge 2 according to one embodiment of the invention. Each of the steps illustrated will be explained with reference to FIGS. 6 to 9.

In the first step 110, the bridge's framework 12 in its initial state is produced using a rapid manufacturing process, which in this process is a selective laser sintering process. As will be understood, the selective laser sintering process comprises using a selective laser sintering machine such as that schematically shown in FIG. 1 and described above, to repeatedly add layers of powdered material to the article 20. A high intensity laser is focussed on the region of the powdered material corresponding to the appropriate shape of the article 20 for the appropriate layer, so as to bind the powder. Subsequently, the surface on which the sintering takes place is lowered, so that when the powdered material is next applied the laser may focus at the same height, but scanned around an appropriate course across the powder.

Figure 6:
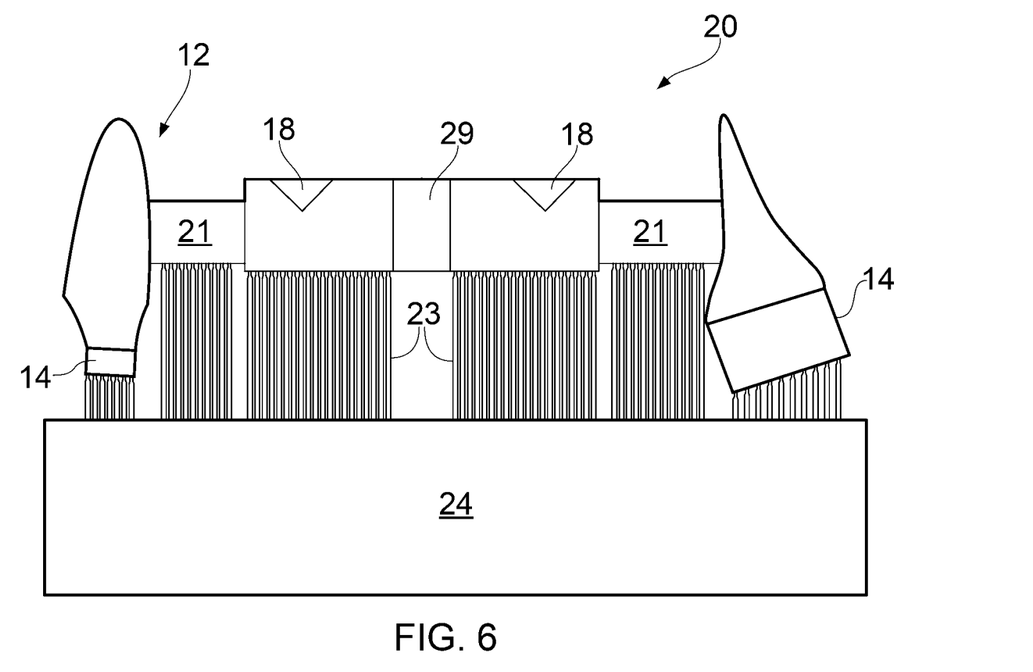
FIG. 6 shows schematically a cross-sectional side view of a laser sintered framework attached to a build plate during manufacture.

FIG. 6 shows an initial state, pre-machined, framework 12 having been constructed by selective laser sintering, but still located on a build plate 24. The figure shows a cross-sectional view of the bridge framework 12. The bridge framework 12 is resting on a support structure 23, which is a web of sintered material of lesser density than the framework 12, but is of sufficient strength to support the bridge framework 12 and to prevent both distortion under its own weight and internal thermal stresses; the support structure 23 is also referred to herein as scaffolding or a support web. As will be understood, although not shown, the build plate 24 may be considerably larger than the bridge framework 12 being produced and as such may permit several bridges 2 to be built simultaneously.

The second step 120 follows the completion of the selective laser sintering process, and comprises removing the build plate 24 and the bridge framework 12 from the selective laser sintering apparatus and preparing them for machining. Preparation can include various optional stages such as placing the bridge framework 12, along with support web 23 and build plate 24 into an industrial oven, in order that a stress relief heat treatment cycle may be conducted. The bridge framework 12 is then removed from the build plate 24 by cutting the support structures 23, with any remaining parts of the structure 23 removed by pliers and abrasive rotary tools. The bridge framework 12 can then be grit blasted to make the entire surface smoother. Even after grit blasting, the side of the bridge framework 12 that was connected to the support structure can sometimes (depending for example on the use of abrasive tools before blasting) still be significantly rougher than the opposite side, due to remnants of the support structure 23 remaining on the bridge. As shown, the excess material 14 to be removed by the machine tool is found on the surface of the article 20 to which the support structure 23 was provided.

As previously stated, the machining of the bridge framework 12 in its initial state can be a multiple stage process, as the bridge framework 12 can require features to be machined from inverse orientations.

Figure 7:
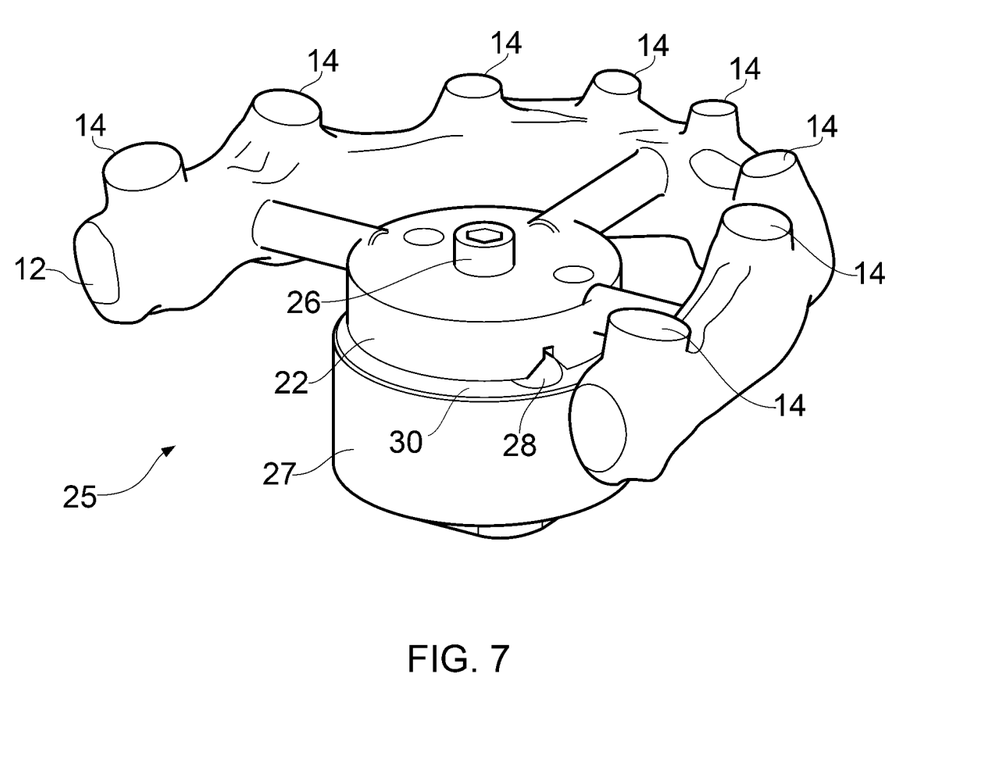
FIG. 7 shows schematically a framework in its initial state clamped using a kinematic mount during manufacture.

As illustrated by FIG. 7, the following step 130 comprises mounting the bridge framework 12 in its initial state onto a mounting structure, in this case clamp 25, in a machine tool apparatus, for example a computer numerically controlled (CNC) milling machine. FIG. 7 shows schematically a view of the article 20 comprising the bridge framework 12 in its initial state clamped into position by the clamp 25 engaging the location hub 22. The clamp 25 comprises a base 27 having three hemispherical protrusions 28 located on its upper surface 30. The protrusions 28 are arranged such that they can engage with the first set of kinematic mount features 18 on the bridge 2, thereby facilitating kinematic mounting of the framework 12 onto the clamp 25. The clamp 25 also comprises an upper clamping member 26 which engages the location hub 22 so as to urge the location hub 22 into the base 27, thereby securely holding the article 20 in place. In this case, the upper clamping member is a screw 26 that extends through a hole 29 in the location hub 22 so that its screw thread (not shown) engages with a cooperating screw thread in the base member 27, and such that as it is tightened, the head of the screw 26 pushes the kinematic features 18 of the location hub 22 into kinematic features 28 of the base 27. The article 20 is clamped such that the surface to be machined is facing upwards.

Figure 8:
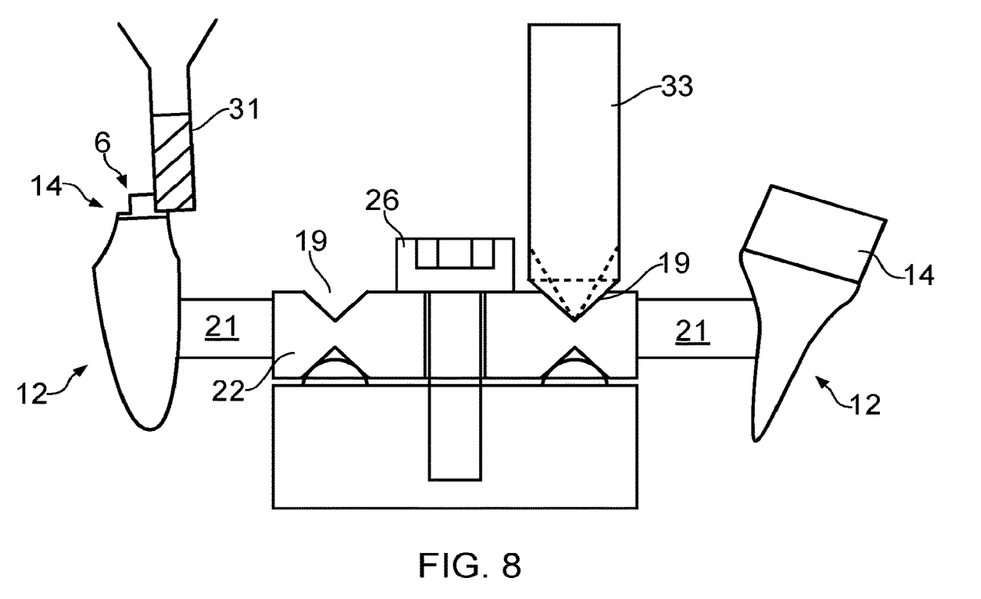
FIG. 8 shows schematically the machining of the implant interfaces during manufacture as well as the machining of kinematic mounting features.

Then at step 140, as shown in FIG. 8, the excess material 14 is machined using a first cutting tool 31 of a computer numerically controlled (CNC) machine tool apparatus in order to form implant interfaces 6. Also, three v-grooves 19 (only two of which are shown) forming a second kinematic mount are milled using a second cutting tool 33 of the CNC machine tool apparatus so as to form them in the location hub 22 (although as will be understood the same first cutting tool could also be used). Although the figure shows the first cutting tool 31 and second cutting tool 33 operating contemporaneously, this need not necessarily be the case. Indeed, it might be that the machine tool apparatus has only one spindle in which case only one tool can be used at any one time.

The location of the excess material portions 14 can be determined simply by virtue of that cooperation between the first set of kinematic mount features 18 and the corresponding kinematic mount features 28 on the clamp's base 27 will have located these features in a known position. Accordingly, there is no need to probe the article 20 in order to determine their location before machining occurs. In particular, in this embodiment the method, and in particular the kinematic features 18, are configured such that the position of the abutments of the framework 12, and more particularly the position of the excess material portions 14, are known within a position tolerance diameter of 100 μm (microns). The accuracy of the laser sintering process can be such that the uncertainty of the position of each abutment of the framework 12 relative to the kinematic mounting features 18 is within a position tolerance diameter of 80 μm (microns) and the position repeatability of the assembly is within a position tolerance diameter of 8 μm (microns). Hence the ratio of i) the uncertainty of the position of each abutment of the framework 12 relative to the kinematic mounting features to ii) the repeatability of the kinematic mount features is 10:1.

Of course, however, such probing could take place if desired, e.g. to confirm location of at least a part of the article, but any such probing operation can be significantly simplified and be much less time consuming as opposed to if such kinematic mounting features 18 were not provided. As will be understood, the machine tool can also receive data or information regarding the location of these features on the article 20. Such data could be bespoke for the article, or could be standard for a plurality of articles. Furthermore, such preformed initial kinematic mount features 18 need not necessarily be provided, in which case if the location of the first features on the article is important (as it is in this case) then an alternative process (e.g. a probing operation) could be used to determine the location of the article within the machine tool's operating volume.

The next step 150 in the method involves removing the framework 12 from the clamp 25, inverting it (e.g. turning it over) and then re-fitting it in the clamp 25 in said inverse orientation. In this orientation, the framework 12 is clamped using the three freshly machined v-grooves 19 forming the second kinematic mount.

Figure 9:
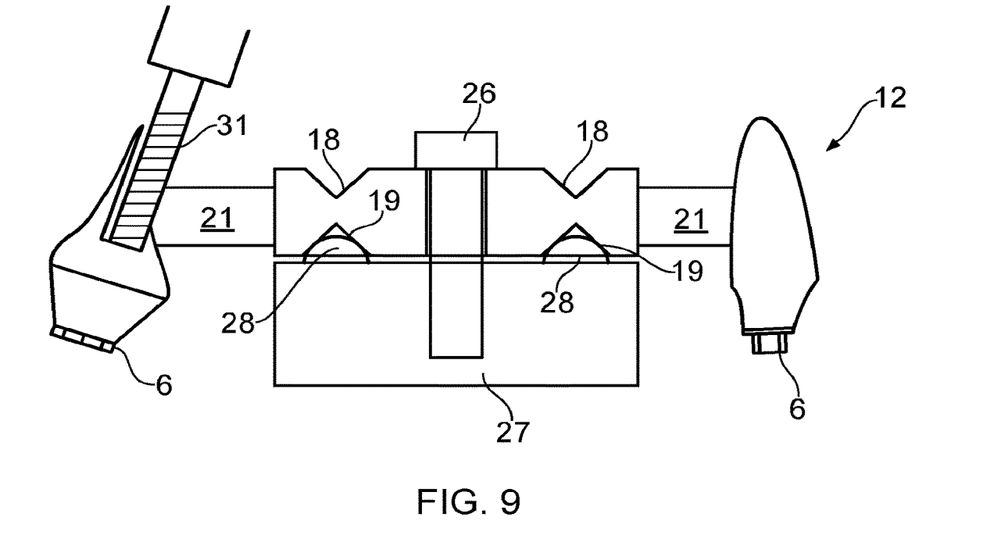
FIG. 9 shows schematically the machining of screw counter bores being machined into the underside of a framework.

The penultimate step 160 in the method, detailed by FIG. 9, involves the second machining stage in which counter bores 8 are machined into the framework 12 using the first cutting tool 31. Furthermore these counter bores 8 will be positioned accurately relative to the implant interface features 6 machined from the excess material 14 due to that the second kinematic mount features 19 were machined during the same first machining stage when the implant interface features were processed. This is important in order to ensure alignment of the counter bores with the implant so as to avoid excess bending forces on the screw connecting the abutment to the implants. In this embodiment the counter bores are entirely formed by the machining step. However, as will be understood, this need not necessarily be the case. For instance, they might have been at least partly formed during the previous additive manufacturing process.

Furthermore, as will be understood, the first and second kinematic mounts 18, 19 are configured such that the article 20 occupies substantially the same machining volume when the article 20 is mounted in the clamp 25 via each of the kinematic mounts 18, 19. In particular, for example, as shown in FIGS. 8 and 9, the volume the product, i.e. the bridge framework 12, occupies when mounted via the first kinematic mount features substantially overlaps (e.g. by at least 50% and in this case by at least 80%) with the volume the product, i.e. the bridge framework 12, occupies when mounted via the second kinematic mount features. Accordingly, this reduces the volume of the machine tool which needs to be calibrated, and reduces the affect of any discrepancy in control or accuracy in the machine tool in different volumes.

The final step 170 comprises removing the framework 12 from the machine tool. The location hub 22 and connectors 21 are detached from the framework 12, and any remains of said connectors are manually ground down. A layer of porcelain 3 can then be added to the framework 12 to form the complete bridge 2 before it is implanted in the patient's jaw.

In the above described embodiment, a first set of kinematic mounting features 18 are formed in the upper surface of the location hub 22 via the laser sintering process. This aids positioned mounting of the article 20 in the machine tool apparatus and can reduce/remove the need for probing of the article 20 to find its position before the machining steps take place. However, this need not necessarily be the case. Indeed, the location of the features formed during the first machining step need not necessarily be precisely controlled. Instead, it might be that only the location of the features formed on the opposite side of the article during the second machining step need be precisely controlled with respect to the features formed during the first machining step. Even if the location of the features formed during the first machining step do need to be accurately controlled, then this can be achieved even without such kinematic features, for instance the position of the article could be probed prior to the first machining step.

In the above described embodiment, the second set of kinematic mount features 19 are formed from scratch during the first machining stage as illustrated by FIG. 8. However, this need not necessarily be the case. For instance, the bulk of the shape of the second set of kinematic features could be formed during the laser sintering process. In this case, they need only be finished using a machine tool during the first machining stage. This would clean up any witnesses of the support structure 23 that would be present on the second set of kinematic mount features 19, as well as enable the machine tool apparatus to know their exact location with respect to features machined during the first machining stage.

FIGS. 10a and 10b, and FIGS. 11a and 11b respectively show underside and top-side views of an article 20' according to another embodiment of the invention made from powdered cobalt-chrome via a laser sintering process which comprises a plurality of individual abutments 12' each of which is attached to a common location hub 22' via a connecting bar 21'. As shown, the lowermost surface of each abutment 12' comprises a circular disk/boss-like protrusion of excess material 14' from which the abutment's 12' implant interface 6' is still to be formed via machining. The figures also show that on one side of the location hub 22', there are provided three v-groove features 18' defining a first kinematic mount. In the same manner as that described above, the three v-groove features 18 can be used to accurately locate the article 20' in a known position and orientation in the machine tool apparatus' volume via the machine tool clamp 25. As also shown, the location hub 22' also comprise two gross-orientation bores 17' extending all the way though the location hub 22'. As described below, these bores 17' can be used to ensure the correct gross orientation of the article 20' in the machine tool clamp 25. In the same manner as described above, when the article 20' is mounted in the clamp 25 via the three v-groove features 18' not only can implant interface features be machined in the excess material portions 14', a second set of three v-groove features defining a second kinematic mount can be machined in the lower side (i.e. on the side opposite to that on which the first of three v-groove features 18 are provided) the location hub during the same first machining process (i.e. whilst the article 20 is mounted via the first kinematic mount provided by the three v-groove features 18). The article 20' can then be flipped over and re-mounted onto the clamp 25 via the newly machined three v-groove features and other features milled on the opposite side of the article 20' (e.g. counter bores 8') the position of which can be accurately located with respect to implant interfaces, even without probing of the article, by virtue of the mounting of the article 20' via the three v-groove features of second kinematic mount formed during the same machining stage in which the interface features were formed. As shown, all of the abutments 12' are oriented such that their longitudinal axes 32 are parallel to each other. Furthermore the abutments and mount are configured such that when the article 20' is mounted in a clamp during subsequent processing, the abutment's longitudinal axis 32, can be parallel to the cutting tool's longitudinal axis.

The invention claimed is:

1. A method of manufacturing an article, comprising:
taking an article formed in an initial state via a first manufacturing process, the article comprising at least one pre-formed initial mounting feature, and performing a second manufacturing process to transform the article into a second state,
wherein the first manufacturing process is an additive manufacturing process and wherein the second manufacturing process comprises:
using the pre-formed initial mounting feature to mount the article in a holding device of a machine for operating on the article,
with the article so mounted in the holding device, processing at least one first feature on the article and processing at least one mounting feature on the article,
re-mounting the article in the holding device via the at least one mounting feature, and
with the article so re-mounted in the holding device, processing at least one second feature on the article.

2. The method as claimed in claim 1, wherein the position of the at least one mounting feature is constrained in a known manner with respect to the at least one first feature, and wherein the position of the at least one second feature is controlled with respect to the at least one first feature using knowledge of the position of the at least one mounting feature with respect to the at least one first feature.

3. The method as claimed in claim 1, wherein the position and orientation of the article in three linear and three rotational degrees of freedom within an operating volume of the machine is known and defined by virtue of an interaction of the at least one mounting feature with the holding device of the machine.

4. The method as claimed in claim 1, wherein the at least one mounting feature comprises kinematic mounting features that are adapted to engage with corresponding kinematic mounting features on the holding device of the machine.

5. The method as claimed in claim 1, wherein the at least one first feature is different to the at least one mounting feature.

6. The method as claimed in claim 1, wherein the at least one first feature is not a mounting feature for mounting the article in the holding device of the machine.

7. The method as claimed in claim 1, wherein the at least one second feature is not a mounting feature for mounting the article in the holding device of the machine.

8. The method as claimed in claim 1, wherein the at least one first feature and the at least one second feature are not mounting features for mounting the article in the holding device of the machine.

9. The method as claimed in claim 1, wherein the at least one second feature and the at least one first feature are located on different faces of the article.

10. The method as claimed in claim 1, wherein the at least one second feature and the at least one first feature are located on substantially opposing faces of the article.

11. The method as claimed in claim 1, wherein re-mounting comprises re-orienting or rotating the article within the machine.

12. The method as claimed in claim 1, wherein the article is mounted in the holding device in a plurality of different orientations during the second manufacturing process, thereby enabling different sides of the article to be processed, even by a tool approaching the article from a same orientation.

13. The method as claimed in claim 1, wherein re-mounting comprises turning the article over.

14. The method as claimed in claim 1, wherein the article occupies substantially the same volume of the machine when the article is mounted for the processing of the at least one first feature and at least one mounting feature and when the article is mounted for the processing of the at least second feature.

15. The method as claimed in claim 1, wherein the article was formed via a laser sintering process.

16. The method as claimed in claim 1, wherein the at least one mounting feature is at least partially formed in the article via the additive manufacturing process.

17. The method as claimed in claim 1, wherein the article comprises an aerospace part.

18. The method as claimed in claim 1, wherein the article comprises an item of jewellery.

19. The method as claimed in claim 1, wherein the at least one mounting feature and the at least one pre-formed initial mounting feature are configured on substantially opposing faces of the article.

20. The method as claimed in claim 1, wherein the at least one pre-formed initial mounting feature and the at least one mounting feature are configured such that the article occupies substantially the same volume of the machine tool apparatus that processes the article when the article is mounted in the holding device via the at least one pre-formed initial mounting feature and via the at least one mounting feature.

21. The method as claimed in claim 1, wherein the second manufacturing process is a subtractive process.

22. The method as claimed in claim 21, wherein the second manufacturing process is a machining process.

23. The method as claimed in claim 1, wherein the article comprises at least one product and at least one member on which the mounting features are provided which is subsequently detached from the at least one product.

24. The method as claimed in claim 23, wherein the article comprises a plurality of products joined together, and which are subsequently separated from each other, and wherein the plurality of products are joined together via the at least one member.

25. The method as claimed in claim 23, wherein at least one member comprises a central hub around which the at least one product is arranged.

26. The method as claimed in claim 1, wherein the article comprises a plurality of products joined together, and which are subsequently separated from each other.

27. The method as claimed in claim 26, wherein the plurality of products comprises a plurality of aerospace parts, a plurality of items of jewellery, or a plurality of medical implants.

28. The method as claimed in claim 27, wherein each of the plurality of medical implants is a dental restoration.

29. The method as claimed in claim 1, comprising performing the additive manufacturing process to form the article in the initial state.

30. The method as claimed in claim 29, comprising forming the article via a laser sintering or laser melting process.

31. The method as claimed in claim 29, comprising building the article layer-by-layer.

32. The method as claimed in claim 31, comprising building the article layer-by-layer from a powdered material.

33. The method as claimed in claim 1, wherein the article comprises a medical implant.

34. The method as claimed in claim 33, wherein the medical implant is a dental restoration.

35. The method as claimed in claim 34, wherein the dental restoration is an implant-supported dental restoration.

36. The method as claimed in claim 34, wherein the dental restoration is a bridge.

37. The method as claimed in claim 34, wherein the dental restoration is a single tooth restoration, such as an implant supported abutment or crown.

38. The method as claimed in claim 34, wherein the at least one first feature and/or the at least one second feature are features which are to interface with another member in a patient's mouth.

* * * * *